United States Patent [19]

Vegoe

[11] Patent Number: 5,002,792

[45] Date of Patent: Mar. 26, 1991

[54] PROCESS FOR MAKING BIOMEDICAL DEVICES UTILIZING THERMOPLASTIC HYDROPHILIC GELS

[75] Inventor: Brett R. Vegoe, Mound, Minn.

[73] Assignee: Medtronic, Inc., Minneapolis, Minn.

[21] Appl. No.: 375,157

[22] Filed: Jul. 3, 1989

Related U.S. Application Data

[63] Continuation of Ser. No. 231,628, Aug. 11, 1988, abandoned, which is a continuation of Ser. No. 907,355, Sep. 15, 1986, abandoned.

[51] Int. Cl.$^5$ ............................................. B05D 5/12
[52] U.S. Cl. ................................... 427/2; 128/639; 264/1.7; 264/36; 264/259; 427/77; 524/916
[58] Field of Search ............... 128/639, 640; 427/2, 427/77; 264/1.5, 1.7, 36, 259; 524/916

[56] References Cited

U.S. PATENT DOCUMENTS

| | | | |
|---|---|---|---|
| 4,317,278 | 3/1982 | Carmon et al. | 128/639 |
| 4,339,295 | 7/1982 | Boretos et al. | 156/275.7 |
| 4,593,053 | 6/1986 | Jeme et al. | 523/111 |

Primary Examiner—James Lowe

[57] ABSTRACT

A method for making biomedical devices employing thermoplastic hydrogels on an operant surface thereof is described. The method generally involves heating a thermoplastic hydrogel to a temperature in the range of 50° C. to about 95° C. to a fluid flowable state, dispensing the fluid hydrogel onto the biomedical device and cooling the hydrogel to a substantially solid state. Microwave heating is preferred.

2 Claims, No Drawings

PROCESS FOR MAKING BIOMEDICAL DEVICES UTILIZING THERMOPLASTIC HYDROPHILIC GELS

This is a continuation of copending application Ser. No. 07/231,628 filed on Aug. 11, 1988 which is a continuation of 06/907,355 filed Sept. 15, 1986, both now abandoned.

This invention relates to methods or processes for making particular biomedical devices. More particularly, this invention relates to methods or processes for making biomedical devices having on an operating or skin-contacting portion or surface thereof thermoplastic, hydrophilic gel sometimes referred to as hydrogel. Yet more particularly, this invention relates to a "hot melt" method for making a biomedical device having on an operant surface thereof a thermoplastic, hydrophilic gel.

BACKGROUND OF THE INVENTION

Numerous U.S. patents describe various biomedical devices which have or which employ on an operant surface thereof a hydrophilic gel sometimes referred to as a hydrogel. For example, recently issued U.S. Pat. No. 4,570,637 in the name of Jevne et al describes a particularly advantageous hydrogel composition for use on biomedical devices. Other hydrogel references of interest include U.S. Pat. No. 3,929,741 (Laskey), U.S. Pat. No. 3,998,214 (Anderson et al), U.S. Pat. No. 4,067,342 (Burton) and the series of patents in the name of Keith et al exemplary of which is U.S. Pat. No. 4,460,562. Such "solid" or "dry" hydrogels have been used on electrodes of various varieties, including iontophoresis electrodes, electocautery ground electrodes and various other medical devices which are intended to be adhered to a patient's skin.

The present invention relates to a method of making certain biomedical devices which employ hydrogels of a particular variety, viz. thermoplastic (as opposed to thermosetting) hydrogels. None of the above references disclose nor suggest the present novel method or process.

BRIEF DESCRIPTION OF THE INVENTION

Briefly, in one aspect, the present invention is a method for making a biomedical device which has, on its operant or operating surface thereof, a preferably tacky thermoplastic hydrogel. Generally speaking, the term "operant surface" or "operating surface" of a biomedical device means that surface intended to be placed in contact with, for example, a patient's skin. However, there may be other reasons why a thermoplastic hydrogel would be employed on a biomedical device that would not necessarily involve contact between the device and human skin. In any of these applications, the term "operant surface" is to be broadly construed to mean adherence or "sticking" of the biomedical device, not only to a patient's skin but perhaps to other surfaces.

In its broadest contemplation, then, the present invention involves heating the thermoplastic hydrogel to a fluid, flowing or flowable state and, while in that state, depositing or dispensing the hydrogel (usually a predetermined or controllable amount) on the operant surface of the biomedical device or a part thereof depending upon the device. Generally the heating step would be accomplished by warming or heating the hydrogel to a temperature in the range of about 50°-100° C., a preferred temperature range of heating being from about 85°-95° C. The temperature selected is generally the lowest at which the hydrogel can be easily dispensed.

Hackh's Chemical Dictionary has defined hydrogel to mean "a gel produced by the coagulation of a colloid with the inclusion of water". This definition generally means high water content gels. For this reason, the heating limitation of approximately 95° C. (at atmospheric pressure) must be carefully observed to avoid generation of excess steam which produces air bubbles and water loss when the hydrogel is deposited. The lower limit of the heating step is defined by the temperature at which the hydrogel becomes fluid and flowable.

It is possible that a thermoplastic hydrogel could be heated to above 95° C., particularly at pressures above atmospheric. As long as the hydrogel is heated to within the temperature range described herein, heating the gel above this range by means of super atmospheric pressure (to avoid water loss and bubble formation) is within contemplation of this invention.

Subsequent to depositing the hydrogel on the operant surface of the desired biomedical device, the hydrogel is permitted to cool to a solid, generally (but not necessarily) tacky state. Since biomedical devices within the contemplation of the present invention are usually intended to be in contact with skin, which is generally at a temperature in the range of approximately 37° C., the cooling step would generally involve cooling to a temperature slightly above 37° C., e.g., in the range of 40° C. to 49° C.

The heating step contemplated herein may be accomplished in any of a number of ways. As described below, a preferred method of heating hydrogel is to place it in a microwave oven. Any other method which heats the hydrogel without changing its characteristics upon resolidification is within the contemplation of this invention.

Subsequent to heating, the thermoplastic hydrogel may be dispensed or deposited by means of essentially any applicator or dispenser known to be useful for dispensing controllable amounts of relatively warm, relatively viscous materials (i.e., "hot melt" applicators). Atmospheric or pressure assisted pumps are contemplated. A preferred dispenser means is an appropriately temperature controlled syringe.

This invention will now be illustrated by the following examples:

EXAMPLE I

A thermoplastic hydrogel for the composition set forth in Table A was synthesized according to processes such as those described in U.S. Pat. No. 4,570,637. This polymerized material then was placed in a temperature controlled syringe. The syringe was placed in a microwave oven and heated at high power with multiple 5 second bursts. In order to ensure uniform heating of the gel, it was necessary to use multiple 5 second bursts along with shorter 3 second bursts such that the hydrogel was heated to a flowable, fluid state.

TABLE A

| Material | % By Weight |
|---|---|
| Polyvinyl Alcohol "Dupont HV" 125,000 molecular weight | 4 |
| Polyvinyl Pyrolidone 360,000 molecular weight | 36 |
| Glycerol | 14 |
| H₂O | 33 |

TABLE A-continued

| Material | % By Weight |
|---|---|
| Lithium Chloride | 13 |

The hot, flowable, fluid plastic hydrogel then was squeezed onto an electrode backing member. Use of the syringe permitted uniform controllable deposition of the hydrogel about and upon the flexible electrode backing member. Using a syringe, this size sample has been found to be workable (i.e., able to be deposited on an electrode) for approximately 2-3 minutes. Since it was contemplated that the electrode would be subsequently handled, a release cover was placed over the fluid gel, the gel being sandwiched between the backing member and the release cover. The completed electrode then was placed in the refrigerator for approximately 2 hours. The actual time that the electrode was cooled is not critical provided it is cooled to a solid, tacky state (if a tacky material is used). At the time of application of the electrode, for example to a patient's skin, the release cover or liner is removed from the gel, and the electrode is pressed into place at a desired location on the patient depending on the intended application.

Alternative to the above method, a syringe of thermoplastic hydrogel may be heated in a conventional oven by a temperature in the range of approximately 90° C. to 120° C. at a time period in the range of approximately 1-3½ hours. Regular checking of the thermoplastic material will be necessary to ensure that it is, in fact, in a flowable state. Subsequent processing remains the same whether the heating step is accomplished by means of a conventional oven or a microwave oven.

The present invention is strictly limited to utilization of thermoplastic (as opposed to thermosetting) hydrogels. The reason for this limitation is that thermosetting hydrogels, by definition, aren't capable of being heating to a plastic, flowable state. Generally speaking, hydrogels which are thermosetting are referred to as "cross-linked" hydrogels. It follows that such cross-linked hydrogels would not be usable within the contemplation of the present invention unless the extent of cross-linking within the hydrogel is so minor as not to preclude the possibility of heating the hydrogel to a plastic, flowable state.

The particular advantages achieved in the practice of the present invention are better control of the amount of hydrogel deposited on biomedical devices and therefore reduction or elimination of waste. Conventionally, hydrogels are polymerized and knife coated onto disposable or reusable backing members for simultaneous or subsequent preparation of electrodes. In their assembly then, the hydrogel (and backing) is cut into the desired shape producing substantial waste material which is discarded. In the practice of the present invention, precise deposition of flowable, thermoplastic hydrogel is permitted. This is important in the first instance to eliminate waste of the hydrogel itself.

This invention is particularly important in the case where, for example, an iontophoresis electrode, wound dressing or passive transdermal drug delivery gel is to be employed. In that example, the hydrogel may be mixed with an expensive drug which is to be iontophoretically delivered. This substantially increases the cost of the hydrogel matrix/drug combination and therefore accentuates the need for a deposition method which lessens or eliminates waste.

Many variations and extensions of the present invention will become obvious in light of the above disclosure. The attached claims are intended to embrace all such variations and extensions and should not be narrowly construed to avoid the spirit and intent of this invention.

What is claimed is:

1. A method for making a biomedical device having a thermoplastic hydrogel on an operant surface thereof comprising the steps of:
   providing a thermoplastic hydrogel comprising polyvinyl alcohol and polyvinyl pyrrolidone;
   providing a biomedical device, or a part thereof having an operant portion which is intended to carry a hydrogel;
   heating the hydrogel to a fluid, flowable state at a temperature in the range of 85° C. to about 95 ° C.;
   depositing the heated hydrogel on the operating surface of the biomedical device, or portion thereof, and permitting the fluid hydrogel to cool a substantially solid state to a temperature in the range of 40° C. to 49° C.

2. A method for making an iontophoresis electrode having a thermoplastic hydrogel on an operant surface thereof comprising the steps of:
   providing a thermoplastic hydrogel comprising polyvinyl alcohol and polyvinyl pyrrolidone;
   providing an ionotophoresis electrode having an operant portion which is intended to carry a hydrogel;
   heating the hydrogel to a fluid, flowable state to a temperature in the range of 85° C. to about 95° C.;
   depositing the heated hydrogel on the operant surface of the iontophoresis electrode, and permitting the fluid hydrogel to cool to a substantially solid state to a temperature in the range of 40° C. to 49° C.

* * * * *